United States Patent [19]

Allain et al.

[11] 4,291,167

[45] Sep. 22, 1981

[54] PREPARATION OF TETRAMETHYLDISILANE FROM 1,2-TETRAMETHYLDICHLORODISILANE

[75] Inventors: Ronald J. Allain, Naperville, Ill.; Joseph P. Maniscalco, Sugar Land, Tex.

[73] Assignee: Nalco Chemical Company, Oak Brook, Ill.

[21] Appl. No.: 172,611

[22] Filed: Jul. 28, 1980

[51] Int. Cl.$^3$ .............................................. C07F 7/08
[52] U.S. Cl. .................................................. 556/430
[58] Field of Search ...................................... 556/430

[56] References Cited

U.S. PATENT DOCUMENTS

| | | | |
|---|---|---|---|
| 3,029,128 | 4/1962 | Chamberlain | 23/14 |
| 3,312,605 | 4/1967 | Braithwaite | 204/59 |
| 3,639,105 | 2/1972 | Atwell et al. | 556/430 X |
| 3,983,224 | 9/1976 | Allain et al. | 423/498 |
| 4,052,430 | 10/1977 | Yajima et al. | 556/430 X |
| 4,146,657 | 3/1979 | Gordon | 427/126 |

FOREIGN PATENT DOCUMENTS 2015983  7/1979  United Kingdom .

OTHER PUBLICATIONS

Schlesinger, "J.A.C.C.", 75, p. 186, 1953.
"J. Organomotac. Chem.", 6, pp. 202–204, 1966.

*Primary Examiner*—Paul F. Shaver
*Attorney, Agent, or Firm*—John G. Premo; Robert A. Miller

[57] ABSTRACT

A process of producing tetramethyldisilane by reacting tetramethyldichlorodisilane with a reducing mixture of NaH and NaBH$_4$ in the presence of a complexing ether such as the diethyl ether of tetraethylene glycol.

5 Claims, No Drawings

PREPARATION OF TETRAMETHYLDISILANE FROM 1,2-TETRAMETHYLDICHLORODISILANE

INTRODUCTION

U.S. Pat. No. 4,146,657, issued to Gordon, teaches the formation of electrically conductive films of tin oxide on substrates such as glass so as to form films having extremely good reflectance of infrared radiation and thereby having importance relating to energy conservation. The films formed in the reference previously mentioned are formed by decomposition of a tin compound which is volatile in the presence of an organic compound containing fluorine, such that the films formed are fluorine containing tin oxide films. These films have a disadvantage in that their refractive index is sufficiently different from the refractive index of the substrate that interference patterns are readily observable when film thickness and other variables of the process are not closely and carefully controlled.

The irridescence observed in these types of coatings can be avoided, as taught in a later reference, United Kingdom Patent No. 2,015,983, which teaches the use of an interlayer of graduated refractive index between the substrate and the final film containing tin oxide or fluorine doped tin oxides. This interlayer of graduated refractive index is formed by intermixing various methylsilane compounds with the alkyl tin compounds used to form the tin coatings.

As taught in the British patent, the tetramethyl tin is less reactive to radicals which are formed during the oxidative/thermally induced decomposition of these mixed compounds than are the reactive methylsilane compounds. Since the tetramethyl tin is less reactive to the radicals formed in the oxidative degradation occurring at the surface of the substrate, it mainly enters into the later stages of the oxidation; and hence, the interlayers of graduated refractive index are formed by intermixing the alkyl tin compounds, preferably tetramethyl tin, with the silane compounds of choice during the formation of these films.

Example 1 of the British patent reference teaches the use of 1,1,2,2-tetramethyldisilane in the formation of these films on a glass substrate which successfully obtains a coated glass which is color-neutral in appearance and which has a visible reflectivity of 15 percent and no visible hazing effects. This film is claimed to have an infrared reflectivity of 90 percent at a 10 micron wavelength. Additional characteristics of these films are illustrated in Great Britain Patent No. 2,015,983 A, which is incorporated herein by reference.

Although the deposition of these films appears to be insensitive to the mixtures of methylsilanes which were attempted, i.e., in Example 2 of this reference, it has been found that the use of purified 1,1,2,2-tetramethyldisilane (hereinafter referred to as TMDS) obtains a better operational process for the continuous coating of a glass substrate having interlayers of graduated refractive index and which contains silicone, tin, and possible fluorine in various molar ratios.

It is therefore important to be able to find a method of manufacturing pure TMDS from relatively inexpensive raw materials. The subject of the instant invention is just such a process. It has been found that pure TMDS can be formed from a prepurified source of tetramethyldichlorodisilane. The reaction involved in the formation of the TMDS is as follows:

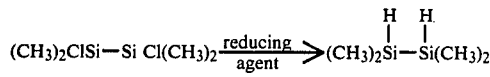

The reducing agents required to accomplish the reaction indicated above have been found to be relatively strong reducing agents such as sodium borohydride, lithium aluminum hydride, etc. The problem is that these reducing agents are very expensive and cannot be readily used in a manner which would yield a commercially viable end product. The subject of this invention includes not only the formation of TMDS but, also, the formation of TMDS by using a commercially viable process which forms the reducing agent required in situ, thereby allowing the use of readily available commercial materials in the process.

THE INVENTION

The subject of the instant invention is a process producing TMDS by:

(a) reacting purified tetramethyldichlorodisilane (hereinafter referred to as TMDCDS) with a substoichiometric mixture of sodium hydride and sodium borohydride in the presence of a complexing ether solvent to produce a mixture of TMDS, unreacted TMDCDS, and a $BH_3$ ether complex; and (b) adding incrementally additional substiochiometric amounts of sodium hydride to this reaction mixture obtained from step (a) in such a manner as to react the sodium hydride with the $BH_3$ ether complex to produce additional sodium borohydride in situ, and (c) allowing the thus-formed sodium borohydride to react in situ with the remaining TMDCDS to produce additional TMDS and the $BH_3$ ether complex, and (d) continuing the sequence of steps (b) and (c) until fully stoichiometric amounts of sodium hydride has been added to the reaction mixture of step (a) so as to complete the reaction converting TMDCDS to TMDS, and (e) separating and recovering the thus-formed TMDS and recovering and recycling the ether solvent and the unreacted sodium hydride and sodium borohydride reactants.

The process described above has been found to be particularly viable when the complexing ether solvent is the diethyl ether of tetraethylene glycol, or the dimethyl and diethyl ethers of other ethylene glycol and polyethylene glycol compounds. These dialkyl capped ethylene glycol and polyethylene glycol ethers have been known for some period of time. As an example, U.S. Pat. No. 3,029,128, which is incorporated herein by reference, teaches the use of the methyl capped ethers obtained from ethylene glycol or various diethylene glycol, triethylene glycol, tetraethylene glycol, etc., oligomers of the ethylene glycol repeating unit.

The preferred solvent for the instant invention is the diethyl ether of tetraethylene glycol, often referred to as DETEG. This ether has been found to have unique solubility characteristics for anhydrous magnesium chloride as taught in U.S. Pat. No. 3,312,605 and 3,983,224.

The process has also been found to require the addition of quantities of sodium hydride and sodium borohydride which are less than stoichiometric amounts when ratioed against the original quantity of purified TMDCDS. It has been found advantageous to use as little as one-tenth of a mole of a mixture of sodium hydride and sodium borohydride when reacting at least one mole of purified TMDCDS in the ether mixture of DETEG. As much as 0.25 moles of a mixture of sodium hydride and sodium borohydride may be used when reacting one mole of the purified TMDCDS in the DETEG solvent ether mixture. The higher the ratio of NaBH$_4$, the faster the reaction proceeds.

The substoichiometric quantities of sodium hydride and sodium borohydride may also include as much as 90% sodium hydride and 10% sodium borohydride (on a mole basis) or as little as 10% sodium hydride and as much as 90% sodium borohydride on the same molar basis. As the sodium borohydride reacts with the purified TMDCDS in the DETEG ether solvent, sodium chloride is formed which precipitates from this ether solution. Therefore, vigorous agitation is required to keep this precipitated material suspended in the reaction mixture.

A byproduct of this reduction, in addition to the sodium chloride formed, is borine, represented by the formula B$_2$H$_6$. This material is present in the mixture of the reaction as the ether complex of its monomeric unit, BH$_3$. This ether complex is often simply designated by the term ether.BH$_3$ complex. This borine complex with the DETEG ether is not sufficiently strong as reducing agent to continue the reaction. Therefore additional quantities of sodium borohydride is necessary to complete the reaction. These quantities are generated in situ by the addition of sodium hydride to the reaction mixture, again in substoichiometric amounts. The reaction of the added sodium borohydride with the ether.BH$_3$ complex regenerates sodium borohydride in situ in such a way that the reduction of TMDCDS continues to form TMDS.

The sequence of steps outlined in the paragraphs above, (b) and (c), is repeated from 4 to 10 times so as to complete the reaction converting the originally charged TMDCDS to TMDS in high yields. Some slight excess of sodium hydride and/or sodium borohydride may remain after complete conversion of the TMDCDS to TMDS.

After the conversion of TMDCDS to TMDS is completed, the recovery of TMDS is accomplished by a fractional distillation in the presence of an inert gas chosen from the group consisting of helium, argon, and nitrogen. The inert gas normally chosen is nitrogen, simply on the basis of its availability and cost. The choice of DETEG as the complexing ether assists in the separation of the TMDS since its boiling point is considerably higher than the boiling point of TMDS, thereby making the recovery of TMDS by fractional distillation in the presence of the inert gas a simple, straightforward procedure.

The Ether Solvents

The ether solvents found to be functional in this reduction reaction forming TMDS are primarily solvents which are dialkylated ethers of ethylene glycol or its oligomers. For example, U.S. Pat. No. 3,029,128, previously incorporated by reference, teaches the use of the methyl capped ethers of ethylene glycol, diethylene glycol, triethylene glycol, and tetraethylene glycol. In this patent, borine is passed through a slurry containing sodium hydride in the dimethyl ether of diethylene glycol under a nitrogen atmosphere. Sodium borohydride is obtained in 94% yield. Other reactions forming both sodium borohydride as well as potassium borohydride are accomplished using exclusively the dimethyl ethers of ethylene glycol, diethylene glycol, triethylene glycol and tetraethylene glycol.

These ethers often have boiling points which correspond to the boiling point of tetramethyldisilane. The isolation of tetramethyldisilane is therefore complicated by the presence of these kind of ethers, commonly referred to as glymes, diglymes, etc.

The use of the diethyl ether of tetraethylene glycol enhances the final desired product and has a beneficial effect on the in situ reaction of sodium hydride with the borine.ether complex forming sodium borohydride in situ and allowing the reduction of the tetramethyldichlorodisilane starting material to the tetramethyldisilane product. It is for these reasons that the diethyl ether of tetraethylene glycol is the ether of choice in this application.

The Tetramethyldichlorodisilanes

The tetramethyldichlorodisilane which is used in the instant invention has been previously synthesized and purified by the following reaction steps.

A sidestream mixture of crude methylchlorodisilane compounds are equilibrated with hexamethyldisilane using a catalyst system of anhydrous aluminum chloride and these reactions are run continuously with both the equilibration reaction occurring simultaneously with a fractional distillation, the middle cut of which contains at least 95% pure 1,2-tetramethyldichlorodisilane. The overheads and bottoms of the distillation are recycled back to the stream of crude methylchlorodisilane for further aluminum chloride redistribution and equilibration reactions.

As a result, the starting material chosen for the instant application is a material which contains at least 95% pure 1,1,2,2-tetramethyldichlorodisilane.

The Reducing Agents

The reaction of various reducing agents with chlorosilanes are well known. The difficulty lies in the fact that the reducing agents required are normally quite expensive. If one were to commercially purchase the materials necessary, the synthesis of the desired tetramethyldisilane compounds would be economically disadvantageous. In an article describing new developments in the chemistry of diborane and the borohydrides, JACS, 75, 186 (1953), the work of Schlesinger and Brown and various collaborators was originally reported. This work was completed to form uranium (IV) borohydrides to examine their utility in the recovery of uranium. Much of this work outlines the reactions of various hydride salts with borane in the presence of some solvent mixtures. This article, which is incorporated herein by reference, teaches the preparation of borohydrides from diborane by an acid-base type reaction, the base being present as the hydride ion. At the time this article was published, the authors had not yet discovered that sodium hydride could react with diborane in the presence of the ether solvents previously mentioned. However, they did teach the reaction of lithium hydride with diborane (B$_2$H$_6$) in the presence of diethyl ether to form lithium borohydride diethyl ether complexes.

Simultaneously, they taught that sodium hydride could not react in a similar fashion since the sodium ions would have a much smaller tendency towards solvation than did the lithium ions in this diethyl ether solvent, and also that sodium borohydride would not be readily soluble in this diethyl ether solvent.

U.S. Pat. No. 3,029,128, previously incorporated by reference, taught the convenient formation of sodium borohydride in the presence of the dimethyl capped ethers of ethylene glycol and its oligomers. Applicants now choose to use the reaction of sodium hydride with diborane which has been generated in situ from the original reduction of TMDCDS with a substoichiometric amount of a mixture of sodium hydride and sodium borohydride, thus forming the desired TMDS compound and a byproduct borane complex with the diethyl ether of tetraethylene glycol.

The addition of quantities of sodium hydride then allows the regeneration, in situ, of sodium borohydride which acts as the reducing agent in the above described reaction.

Since applicants start with a pure form of tetramethyldichlorodisilane, and the reaction of sodium borohydride formed in situ by the reaction of sodium hydride with borane.DETEG complexes is a high yield reaction, and since the DETEG solvent system is a high boiling solvent allowing recovery of pure tetramethyldisilane, applicants feel that the combination of these steps is unique to the production of TMDS.

THE EXAMPLES

1. Into a 20 gallon Pfaudler reactor with an inert gas purge, 1.66 kilograms of 57% sodium hydride in mineral oil and 0.34 kilograms of sodium borohydride was loaded. 10 gallons of dried DETEG was then pumped into the reactor. Agitation was set at 400 revolutions per minute. Over a two-hour period, 3.68 kilograms of 1,1,2,2-tetramethyldichlorodisilane, which has been previously purified to a purity of at least 95 weight percent, was added.

After 6 hours of agitation, a 70% yield of tetramethyldisilane was obtained. The contents of the reactor were then pumped into a second reactor containing 5 gallons of chilled water. The organic layer was repeatedly water-washed until all of the DETEG was removed. The tetramethyldisilane purity was approximately 70% in a mixture of mineral oil and toluene. (The toluene was derived as an impurity from the DETEG used.)

This mixture was then distilled to obtain tetramethyldisilane of approximately 98% purity. The distillation apparatus consisted of a 3-foot tall, 1-inch ID, column packed with stainless steel protruded packing and equipped with a magnetic distilling head. By varying the reflux rates in a fashion known in the art, high purity TMDS was obtained.

2. A reaction of similar nature to Example 1 could be carried out in such a way as to yield the 1,1,2,2-tetramethyldisilane. The contents of the reactor could then be filtered to remove the sodium chloride precipitated as a byproduct from this reaction, and then the filtrate could easily be distilled to recover tetramethyldisilane and allow the recycle of the DETEG.

3. The tetramethyldisilane material produced and recovered as taught in Example 1 was submitted to an outside laboratory for analysis. The analysis obtained is reported in Table 1.

TABLE I

| SPECIFIC GRAVITY @ 60/60° F. | | 0.7260 | |
|---|---|---|---|
| VAPOR PRESSURE @ 100° F. | | 2.2# | |
| FLASH POINT, TAG CLOSED CUP | | BELOW 20° F. | |
| VISCOSITY, KINEMATIC @ 60° F. | | 0.25 C.S. | |
| VISCOSITY, ABSOLUTE @ 60° F. | | 0.19 C.P. | |
| DISTILLATION | | | |
| INITIAL BOILING POINT | 182° F. | END POINT | 222 |
| 5% RECOVERED @ | 183 | RECOVERY | 98% |
| 10% RECOVERED @ | 185 | RESIDUE | 1.0% |
| 20% RECOVERED @ | 185 | LOSS | 1.0% |
| 30% RECOVERED @ | 186 | 10% | |
| 40% RECOVERED @ | 186 | EVAPORATED @ | 185 |
| 50% RECOVERED @ | 186 | 50% | |
| 60% RECOVERED @ | 186 | EVAPORATED @ | 186 |
| 70% RECOVERED @ | 187 | 90% | |
| 80% RECOVERED @ | 188 | EVAPORATED @ | 188 |
| 90% RECOVERED @ | 190 | | |
| 95% RECOVERED @ | 206 | | |

Having thus described our invention, it is claimed as follows:

1. A process of producing TMDS by:
   (a) reacting purified TMDCDS with a substoichiometric mixture of NaH and NaBH$_4$ in the presence of a complexing ether solvent to produce TMDS and a BH$_3$.ether complex, and
   (b) adding incrementally additional substoichiometric amounts of NaH to the reaction mixture obtained from step (a) to react with the BH$_3$.ether complex to produce NaBH$_4$, and
   (c) allowing the thus-formed NaBH$_4$ to react in situ with the remaining TMDCDS to produce TMDS and a BH$_3$.ether complex, and
   (d) continuing the sequence of steps (b) and (c) until fully stoichiometric amounts of NaH have been added to the reaction mixture of step (a), so as to complete the reaction converting TMDCDS to TMDS, and
   (e) separating and recovering the thus-formed TMDS and recovering and recycling the ether solvent and the unreacted NaH and NaBH$_4$ reactants.

2. The process of claim 1 wherein the complexing ether solvent is the diethyl ether of tetraethylene glycol.

3. The process of claim 1 wherein the substoichiometric mixture of NaH and NaBH$_4$ in step 1(a) and the substoichiometric amounts of NaH added incrementally in step 1(b) is between 0.10 to 0.25 of the total moles of purified TMDCDS present in original step 1(a).

4. The process of claim 1 wherein the steps (b) and (c) are repeated from four to ten times so as to complete the reaction converting TMDCDS to TMDS.

5. The process of claim 1 wherein the recovery of TMDS is completed by fractional distillation in the presence of an inert gas chosen from the group consisting of helium, argon and nitrogen.

* * * * *